United States Patent [19]

Holtsch

[11] Patent Number: 4,899,905

[45] Date of Patent: Feb. 13, 1990

[54] DISPENSING CONTAINER WITH SMALL PREMOISTURIZED CLOTHS

[75] Inventor: Ernst P. Holtsch, Taunusstein-Wingsback, Fed. Rep. of Germany

[73] Assignee: Holtsch Metallwarenherstellung, Taunusstein-Wingsbach, Fed. Rep. of Germany

[21] Appl. No.: 90,227

[22] Filed: Aug. 27, 1987

[30] Foreign Application Priority Data

Feb. 7, 1987 [DE] Fed. Rep. of Germany ....... 8701838

[51] Int. Cl.$^4$ .............................................. B65H 1/00
[52] U.S. Cl. ...................................... 221/63; 221/33
[58] Field of Search .................. 221/63, 50–59, 221/61, 62, 48, 47, 33, 38; 206/233, 812, 820; 225/32, 106

[56] References Cited

U.S. PATENT DOCUMENTS

| | | | |
|---|---|---|---|
| 2,514,612 | 7/1950 | Snow | 221/48 X |
| 2,823,089 | 2/1958 | DeFrance | 221/63 X |
| 3,161,336 | 12/1964 | Loescher | 221/63 X |
| 3,780,908 | 12/1973 | Fitzpatrick et al. | 221/48 |
| 4,017,002 | 4/1977 | Doyle et al. | 221/63 |
| 4,138,034 | 2/1979 | McCarthy | 221/63 X |
| 4,156,493 | 5/1979 | Julius | 221/63 |
| 4,159,772 | 7/1979 | Beck | 221/63 X |
| 4,180,160 | 12/1979 | Ogawa et al. | 221/63 X |
| 4,219,129 | 8/1980 | Sedgwick | 221/63 |
| 4,328,907 | 5/1982 | Beard | 221/63 |
| 4,353,480 | 10/1982 | McFadyen | 221/63 |
| 4,534,491 | 8/1985 | Norton et al. | 221/63 |
| 4,651,895 | 3/1987 | Niske et al. | 221/63 |

FOREIGN PATENT DOCUMENTS

| | | | |
|---|---|---|---|
| 7900371 | 7/1980 | Netherlands | 221/63 |
| 1382183 | 1/1975 | United Kingdom | 221/63 |
| 1419167 | 12/1975 | United Kingdom | 221/63 |
| 1438240 | 6/1976 | United Kingdom | 221/63 |

Primary Examiner—Joseph J. Rolla
Assistant Examiner—Edward S. Ammeen
Attorney, Agent, or Firm—Michael J. Striker

[57] ABSTRACT

A container with a strip of continuous premoisturized swabs therein, each swab being rectangular and interconnected with adjacent swabs at their respective corners. The swabs are folded only at their interconnection location and stacked one on top of the other. The container has an end face with an opening, through which a portion of the uppermost swab extends. The container also has a lid to protect the portion of the uppermost swab extending through the opening. Each swab is removable individually by pulling vertically on the portion of the uppermost swab until it tears at the interconnection location with the successive swab, because of frictional resistance generated by accumulation of the successive swab in the opening being greater than the tear strength of the interconnection location.

10 Claims, 2 Drawing Sheets

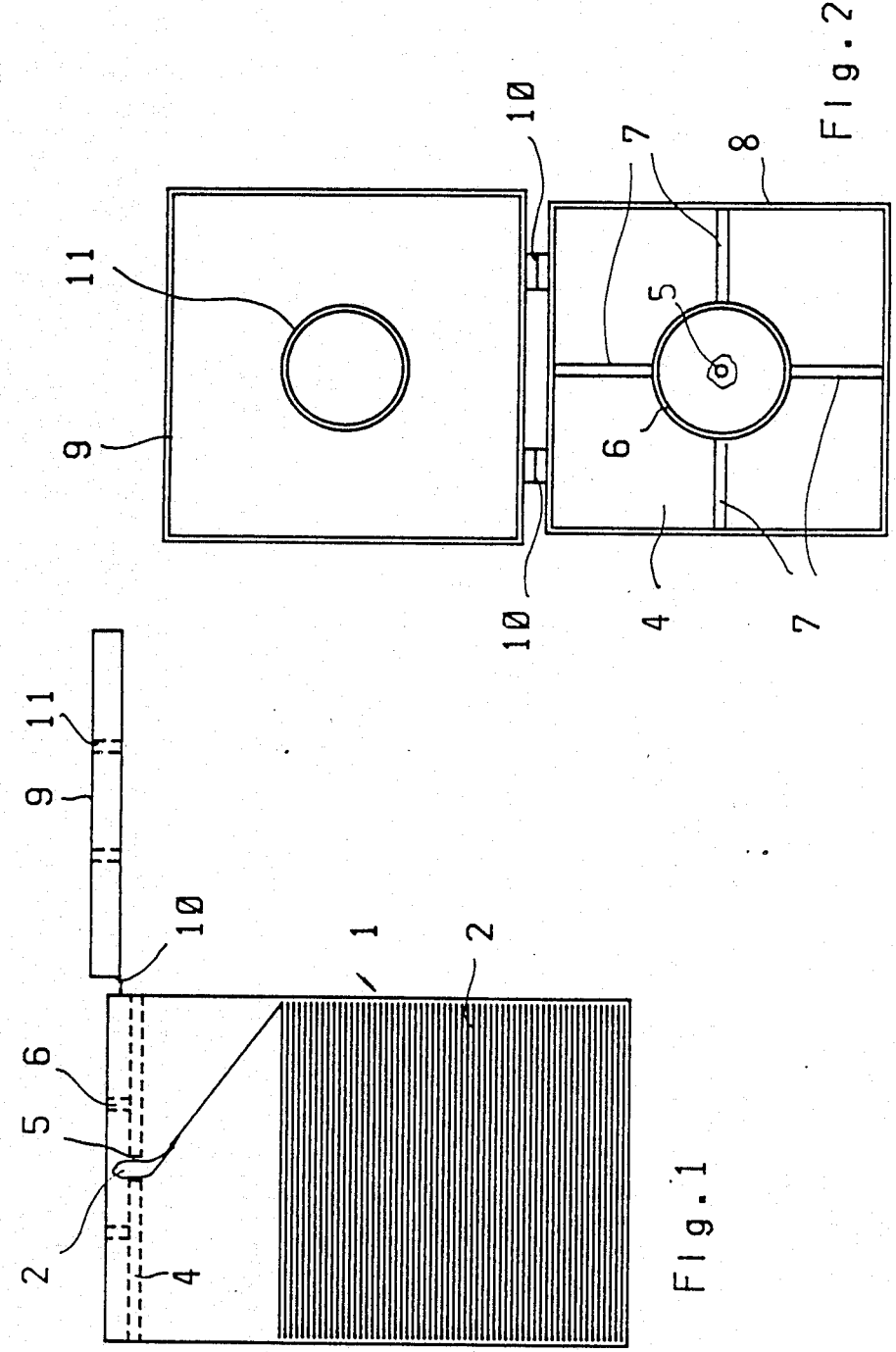

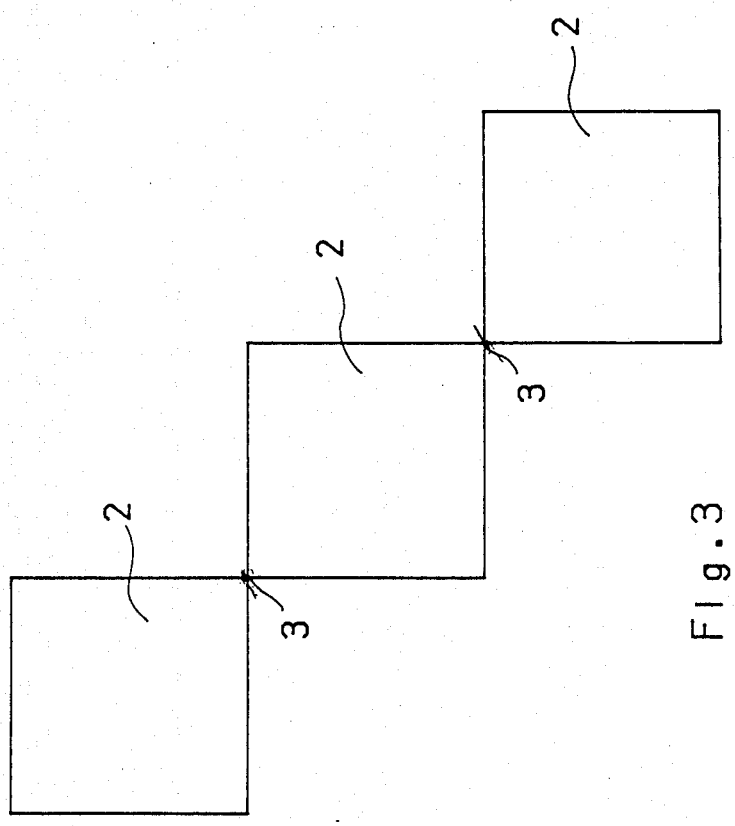

DISPENSING CONTAINER WITH SMALL PREMOISTURIZED CLOTHS

BACKGROUND OF THE INVENTION

The present invention relates generally to a dispensing container with small premoisturized cloths, especially where the cloths are swabs impregnated with an anti-septic and stacked in folded form in the container. Each swab is formed to be pulled out one after the other through an opening in the container.

One type of dispensing container is known from DE-OS 24 05 793, in which premoisturized cloths are separated by transverse perforations or notches and extend through an opening. Projections extend along the edge of the opening for engagement in the perforations or notches in the cloths so as to permit one cloth at a time to be severed. This type of container therefore requires that each individual cloth be vertically drawn exactly against the projections in the opening in order to obtain reliable severing. Otherwise, severing of one cloth from the next may fail to take place.

Another type of dispensing container is known from U.S. Pat. No. 2,823,089 (De Franco 1956) in which a plurality of rectangular tissues are connected to each other at two diagonally opposite corners. The tissues are folded to appear as stacked isosceles trapezoids to enable a portion of the uppermost tissue to be pulled through a slot, the slot being adjacent to an edge of the container. The uppermost tissue will always have a portion extending through the slot.

Each tissue is pulled out of the container individually, because the tissues separate in the connection area between tissues when the edges of the successive tissue engages the edges of the slot, building up resistance that exceeds the tearing strength of the connection area.

However, the portion of the uppermost tissue that extends through the slot is subject to contamination, which is undesireable in environments requiring optimal sterilization.

SUMMARY OF THE INVENTION

It is the object of the present invention to provide a dispensing container with small premoistened swabs to permit reliable individual and successive withdrawl and separation of small premoisturized cloths, particularly where the swabs are impregnated with an anti-septic such as alcohol.

In keeping with this object, and others which will become apparent hereinafter, one aspect of the invention resides, briefly stated, in a combination of a dispensing container and strip of cloths in the container. The strip of cloths are a continuous strip of predetermined cloths formed as adjacent rectangles each with two corners diagonally opposite from each other, the adjacent rectangles interconnecting with each other only at the corners. The adjacent rectangles are folded in the region of their corners so as to form a stack of rectangles one on top of the other. The combination also has a dispensing container housing the stack. The container has an end face with edges as well as an opening spaced away from the edges. The stack has an uppermost rectangle having a corner portion in the region of one of its corners extending through the opening. The combination also has means for protecting the corner portion from contamination and including a lid hinged to the container to removably enclose the corner portion entirely.

It is another object of the invention to releasbly engage the lid and end face together by a continuous flange that engages one of the lid and the end face of the container.

It is a further object to protect the corner portion of the uppermost cloth by enclosing the same between an interengaging collar and capsule, which are formed on the end face and lid respectively.

It is an additional object to provide four ridges on the end face in which each ridge extends from the collar to the flange.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is a side elevational view of a container with interconnected swabs that are folded and stacked therein according to present invention with the lid of the container in the open position.

FIG. 2 is a top plan view of FIG. 1.

FIG. 3 is a top view of three interconnected swabs before being folded and stacked into the container.

DETAILED DESCRIPTION OF THE PREFERRED EMBODIMENT

Referring now to the drawings, FIG. 1 shows a container in the form of a small rectangular box 1 in which swabs 2 are stacked in a folded fashion. The individual swabs 2 are each rectangular or square, and have a size substantially corresponding to the size of the box as shown in FIG. 1. The swabs are interconnected at two diagonally opposed corners 3, and symmetrical relative to a line extending through the corners of all swabs, as shown in FIG. 3. The interconnection is made either directly or by a narrow web.

An end wall or end face 4 at the top of the box 1 is formed with a circular opening 5. The respective uppermost swab 2 extends through this opening 5. Advantageously, this opening 5 is centrally located in the end wall 4 spaced away from the edges, so that a lid 9 can be connected to protect the portion of the uppermost swab 2 extending through the opening 5.

Circular opening 5 is surrounded by a cylindrical collar 6 from which four ridges 7 extend towards a flange 8 provided at the top. Flange 8 is continuous and forms a rectangle that has two sets of parallel walls. Each ridge 7 extends parallel to one set of the parallel walls of the flange 8. Lid 9 is connected to box 1 by two flexible hinges 10 formed as thinned portions of a suitable synthetic resin or plastic material. The lid 9 can therefore be swung on the end wall 4 about the flexible hinges 10. A cylindrical capsule 11 on the inside of lid 9 fits inside of collar 6 when lid 9 is swung onto the end wall 4 to close the same tightly and enclose the portion of the uppermost swab 2 extending through opening 5, providing protection against contamination.

In order to separate the uppermost swab 2 from a successive swab inside box 1, the portion of uppermost swab 2 extending through opening 5 is pulled upward, forcing the uppermost swab 2 entirely out of the box 1, until the interconnection with the successive swab 2 tears because the frictional resistance of the successive swab 2 increases due to material of the successive swab accumulating in opening 5. However, enough of the successive swab 2 is pulled out before tearing takes place to facilitate its own subsequent removal.

It may be desireable to sterilize the swabs 2 by cobalt radiation so that the container should be made from materials which remain intact and do not deform when exposed to gamma radiation. This is of concern for hinge 10 must be both flexible and durable as well. It is recommeded to use a polypropylene homopolymer material that is gamma radiation resistant, e.g. Neste Chemicals polypropylene PD 921 as developed by Herkules, an American corporation.

Box 1 need not have a rectangular cross-section, but may have, for example, a circular cross-section. Further, an isosceles trapezoidal-shaped notch can be formed on one edge of the lid 9 to facilitate opening the lid. This notch is located opposite the edge of the lid that is hinged to the box 1.

Box 1, lid 9, collar 6, capsule 11, and ridges 7 are all ideally made out of the same synthetic resin or plastic material. It is advantageous for such material to be transparent, so that one can readily observe how many swabs 2 remain inside box 1 and are readily available for use. Since the swabs are each folded to retain their rectangular appearance as opposed to appear to have some other configuration, an otherwise possible miscount or confusion as to shape and size is avoided.

Further, the rectangular cross-section of the box 1 and the lid 1 can be of the same dimensions. In such a construction, the continuous flange 8 extends upward from the end face 4 within a border defined by the edges of the end face 4 so as to sealably engage with the edges of the lid 9 when the lid 9 is closed on end face 4. While the preferred embodiment places the capsule 11 on the lid 9, and the collar 6, and flange 8 on the end face 4, the arrangement can be switched such that the collar, flange are on the lid 9 and the capsule is on the end face 4.

It will be understood that each of the elements described above, or two or more together, may also find a useful application in other types of container and cloth combinations differing from the types described above.

While the invention has been illustrated and described as embodied in a container and cloth combination, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for the various applications without omitting features that, from the standpoint of prior art, fairly constitute essential characteristics of the generic or specific aspects of this invention.

What is desired to be protected by Letters Patent is set forth in the appended claims.

I claim:

1. A dispenser comprising:
   a continuous strip of liquid impregnated swabs formed as adjacent rectangles each having two corners diagonally opposite each other, said adjacent rectangles interconnecting with each other only at said two corners, said rectangles being symmetrical relative to a line extending through said two corners of all of said rectangles in an unfolded position of said strip, every adjacent two of said adjacent rectangles being folded only in a region of said corners between said adjacent rectangles so as to form a stack of said adjacent rectangles one on top of each other;
   a dispensing container housing said stack and having an inner size corresponding to a size of each of said rectangles, said container having an end face with peripheral edges, said end face being formed with an opening spaced inwardly away from said peripheral edges and located centrally of said end face, said stack including an uppermost one of said rectangles with a corner portion extending through said opening, said opening having a width approximately the size of a corner region of said adjacent rectangles immediately adjacent to the corners and being narrower than a diagonal width of said adjacent rectangles so as to resist passage of said adjacent rectangles from being pulled through said opening and thereby cause said adjacent rectangles to separate from each other at said region of said corners; and
   means for protecting said corner portion from contamination, said protecting means including a lid hinged to said container to removably enclose said corner portion entirely.

2. The dispenser of claim 1, wherein said face has a central area, said opening being arranged in said central area.

3. The dispenser of claim 1, wherein said opening is circular.

4. The dispenser as defined in claim 1, wherein all of said container and said protecting means are formed of synthetic resin.

5. The dispenser as defined in claim 1, wherein said swabs are each impregnated with an anti-septic.

6. The dispenser as defined in claim 5, wherein said anti-septic is alcohol.

7. A dispenser comprising:
   a continuous strip of liquid impregnated swabs formed as adjacent rectangles each having two corners diagonally opposite each other, said adjacent rectangles interconnecting with each other only at said corners, every adjacent two of said adjacent rectangles being folded only in a region of said corners between said adjacent rectangles so as to form a stack of said adjacent rectangles one on top of each other;
   a vertical dispensing container housing said stack, said container having an end face with peripheral edges, said end face being formed with an opening spaced away from said peripheral edges, said stack including an uppermost one of said rectangles with a corner portion extending through said opening, said opening being narrower than a diagonal width of said adjacent rectangles so as to resist passage of said adjacent rectangles from being pulled upwardly through said opening of said end face and thereby causing said adjacent rectangles to separate from each other at said region of said corners;
   means for protecting said corner portion from contamination, said protecting means including a lid hinged to said container to removably enclose said corner portion entirely by pressing said lid downwardly toward said end face and a continuous flange provided on said end face of said dispensing container at said peripheral edges and releasably engaging with said lid, said lid having an inner surface provided with a capsule while said end face of said dispensing container having a collar disposed between said opening and said flange and releasably engaging with said capsule; and means for reinforcing said end face against forces produced during an upward pulling of said rectangles through said opening of said end face and during a downward pressing of said lid toward said end face, said reinforcing means including a plurality of ridges provided on said end face of said dispensing container and extending from said collar to said flange.

8. The dispenser as defined in claim 7, wherein said capsule and said collar each are formed cylindrical.

9. A dispenser comprising:

a continuous strip of liquid impregnated swabs formed as adjacent rectangles each having two corners diagonally opposite each other, said adjacent rectangles interconnecting with each other only at said corners, every adjacent two of said adjacent rectangles being folded in a region of said corners between said adjacent rectangles so as to form a stack of said adjacent rectangles one on top of each other;

a vertical dispensing container housing said stack, said container having an end face with peripheral edges, said end face being formed with an opening spaced away from said peripheral edges, said stack including an uppermost one of said rectangles with a corner portion extending through said opening, said opening being narroer than a diagonal width of said adjacent rectangles so as to resist passage of said adjacent rectangles from being pulled upwardly through said opening of said end face and thereby causing said adjacent rectangles to separate from each other at said region of said corners; and means for protecting said corner portion from contamination, said protecting means including a lid hinged to said container to removably enclose said corner portion entirely, said dispensing container being formed of a material that remains intact and does not deform from exposure to sterilization radiation so that exposing said stack housed in said dispensing container to said sterilizing radiation sterilizes said stack without deforming said dispensing container.

10. A dispenser comprising:

a continuous strip of liquid impregnated swabs formed as adjacent rectangles each having two corners diagonally opposite each other, said adjacent rectangles interconnecting with each other only at said two corners, said rectangles being symmetrical relative to a line extending through said two corners of all said rectangles in an unfolded position of said strip, every adjacent two of said adjacent rectangles being folded only in a region of said corners between said adjacent rectangles so as to form a stack of said adjacent rectangles one on top of each other;

a rectangular dispensing container housing said stack and having an inner size corresponding to a size of each of said rectangles, said container having an end face with peripheral edges, said end face being formed with an opening spaced inwardly away from said peripheral edges and located centrally of said end face, said stack including an uppermost one of said rectangles with a corner portion extending through said opening, said opening having a width approximately the size of a corner region of said adjacent rectangles immediately adjacent to the corners and being narrower than a diagonal width of said adjacent rectangles so as to resist passage of said adjacent rectangles from being pulled through said opening and thereby cause said adjacent rectangles to separate from each other at said region of said corners; and means for protecting said corner portion from contamination, said protecting means including a lid hinged to said container to removably enclose said corner portion entirely.

* * * * *